US00PP29750P2

(12) United States Plant Patent
Kamerman

(10) Patent No.: US PP29,750 P2
(45) Date of Patent: Oct. 16, 2018

(54) ***CLUSIA* PLANT NAMED 'LICLUS02'**

(50) Latin Name: ***Clusia rosea* (L.)**
Varietal Denomination: LICLUS02

(71) Applicant: Handelsonderneming Licro, Uithoorn (NL)

(72) Inventor: Johan Albert Kamerman, Uithoorn (NL)

(73) Assignee: Handelsonderneming Licro, Uithoorn (NL)

( * ) Notice: Subject to any disclaimer, the term of this patent is extended or adjusted under 35 U.S.C. 154(b) by 0 days.

(21) Appl. No.: 15/731,919

(22) Filed: Aug. 23, 2017

(51) Int. Cl.
*A01H 5/00* (2018.01)

(52) U.S. Cl.
USPC ..... Plt./226

(58) Field of Classification Search
USPC ..... Plt./226
CPC ... A01H 5/00; A01H 5/04; A01H 5/12; A01H 6/00
See application file for complete search history.

*Primary Examiner* — June Hwu
(74) *Attorney, Agent, or Firm* — Samuel R. McCoy, Jr.

(57) ABSTRACT

A new and distinct *Clusia rosea* cultivar named 'LICLUS02' which is characterized by a broad and upright growth habit, obovate plant form, moderately free branching, large medium green leaves that are very narrowly margined yellow-green, and the stability of these characteristics from generation to generation.

2 Drawing Sheets

Latin name of the genus and species: The Latin name of the genus and species of the novel variety disclosed herein is *Clusia rosea* (L.).

Variety denomination: The inventive variety of *Clusia rosea* disclosed herein has been given the variety denomination 'LICLUS02'.

BACKGROUND OF THE INVENTION

Parentage: 'LICLUS02' is the result of a spontaneous whole-plant mutation of *Clusia rosea* 'Princess' (not patented in the United States; Community Plant Variety Office Grant No. EU8456) which was discovered at the inventor's commercial greenhouse in Uithoorn, the Netherlands in January of 2016 and was ultimately selected for commercialization due to its compact size and large medium green leaves.

Asexual Reproduction: Asexual reproduction was initiated in March of 2016, by way of meristematic tissue culture, in Uithoorn, the Netherlands. Through two subsequent generations, the unique features of this cultivar have proven to be stable and true to type.

SUMMARY OF THE INVENTION

The cultivar 'LICLUS02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LICLUS02'. These characteristics in combination distinguish 'LICLUS02' as a new and distinct *Clusia rosea* cultivar:

1. 'LICLUS02' is a moderately branched, compact plant; and
2. 'LICLUS02' exhibits medium green leaves that are very narrowly margined yellow-green; and
3. 'LICLUS02' exhibits large leaves.

BOTANICAL DESCRIPTION OF THE PLANT

Figure 1:
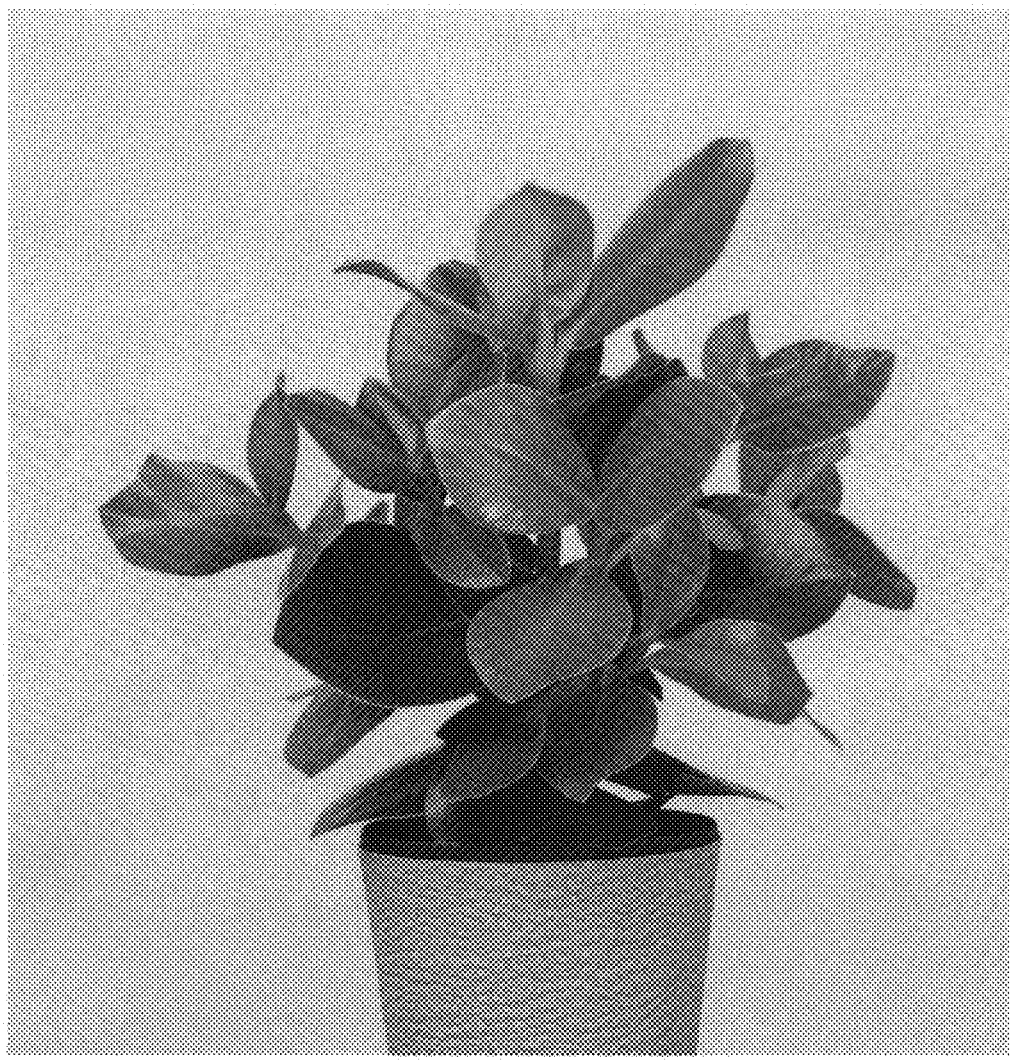
FIG. 1 illustrates, as nearly true as it is reasonably possible to make the same in color photographs of this type, an exemplary plant of 'LICLUS02' grown in a commercial greenhouse in Uithoorn, the Netherlands. This plant is approximately 6 months old, shown planted in a 12 cm nursery container.
Figure 2:
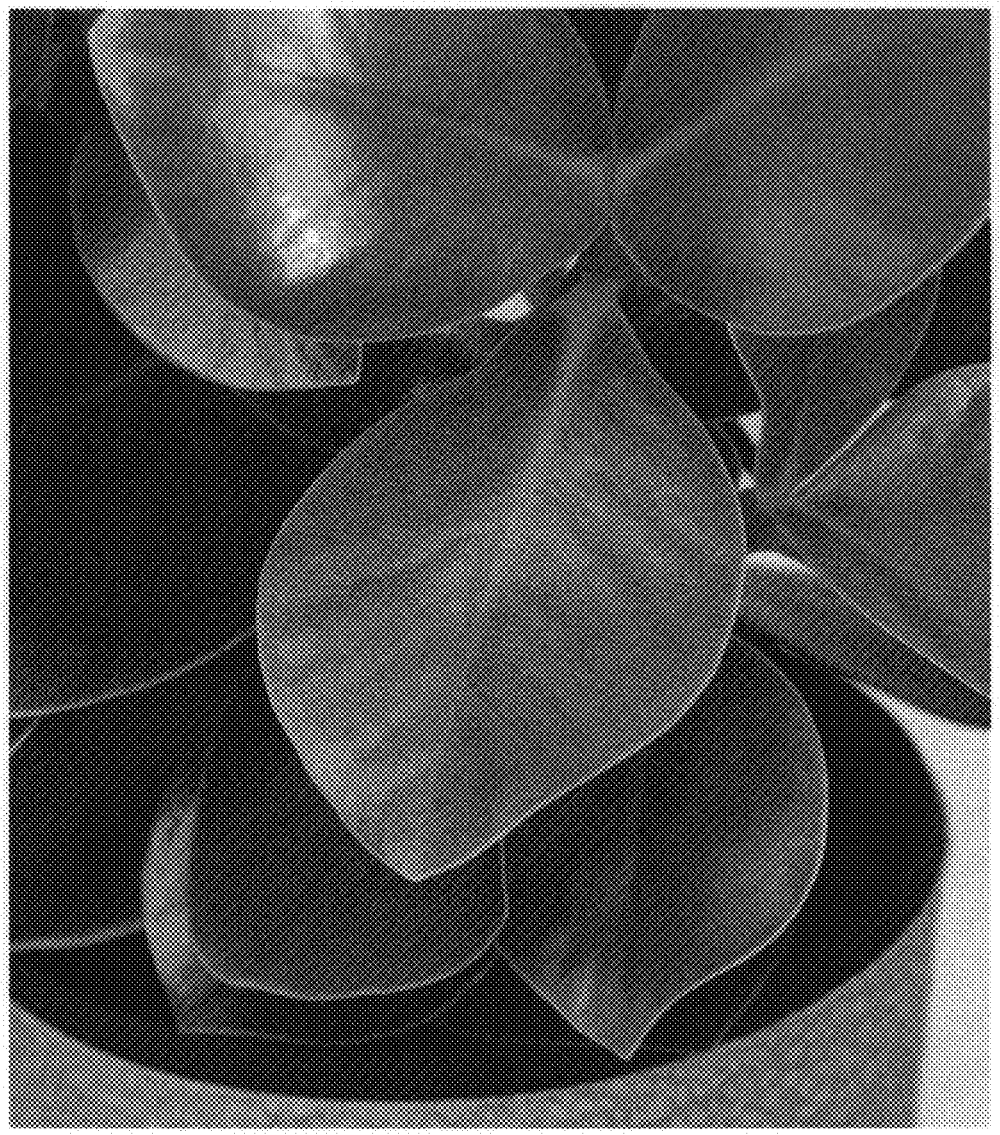
FIG. 2 illustrates, as nearly true as it is reasonably possible to make the same in color photographs of this type, the typical mature foliage habit of 'LICLUS02'.

The following observations and measurements made in August of 2017 describe averages from a sample set of six specimens of 6 month old 'LICLUS02' plants grown in 12 cm nursery containers at a commercial greenhouse in Uithoorn, the Netherlands. Plants were produced without the use of pest or disease control measures, and also without applying any fertilizer. Plants were grown under indirect sunlight and no photoperiodic treatments or artificial light was given to the plants. Irrigation was provided by way of flood benches.

Those skilled in the art will appreciate that certain characteristics will vary with older or, conversely, with younger plants. 'LICLUS02' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LICLUS02' and a comparison with the parent and closest known comparator, *Clusia rosea* 'Princess', is provided below.

Plant description:

*Growth habit*.—Broad, upright growth habit.

*Plant form*.—Obovate.

*Height from soil level to top of foliar plane*.—26.6 cm, on average.

*Plant diameter*.—Average of 27.5 cm.

*Growth rate*.—Low to moderate.

*Plant vigor*.—Moderate.

*Propagation*.—Type — Meristematic tissue culture. Time to initiate roots — Approximately 40 days at 21 degrees Celsius. Crop time — No less than 6 months, depending on the size of the container.

*Disease and pest resistance or susceptibility*.—Plants have not been observed to be susceptible or resistant to pathogens and pests common to *Clusia*.

*Environmental tolerances*.—Adapt to, at least, USDA Zones 10 to 13 and temperatures as high as 40 degrees Celsius; moderate tolerance to wind and rain.

Root system:

*General description*.—Small, fleshy, free-branching roots.

Stems:

*Branching habit*.—Basal branching, with one primary stem and eight lateral branches, on average; freely branching. All stems and branches produce a green-white (no corresponding R.H.S. color) milky substance when damaged.

*Dimensions*.—Primary stem varies with age; oldest lateral branch is 8.8 cm long and 0.6 cm in diameter with an internode length of 3.5 cm, on average.

*Cross section*.—Rounded.

*Texture and luster*.—Glabrous and slightly glossy.

*Aspect*.—60 degrees from vertical.

*Strength*.—Strong.

*Color, juvenile*.—Yellow-green, RHS 144C.

*Color, mature*.—Yellow-green, RHS 144A.

*Color at internodes*.—Yellow-green, RHS 144A.

Foliage:

*Compound or simple*.—Simple.

*Arrangement*.—Opposite.

*Attachment*.—Petiolate.

*Quantity*.—Approximately 6 leaves per lateral branch.

*Shape*.—Broad elliptical to broad obovate.

*Dimensions*.—9.2 cm long by 7.8 cm wide, on average.

*Aspect*.—Flat; midrib is very slightly carinate.

*Apex*.—Broad acute.

*Base*.—Obtuse to very short attenuate.

*Margin*.—Entire; not undulated.

*Pubescence, texture and luster of adaxial surface*.—Glabrous, leathery, and glossy.

*Pubescence, texture and luster of abaxial surface*.—Glabrous, leathery, and moderately glossy.

*Color*.—Juvenile foliage, adaxial surface — Green, nearest to RHS 143A, and very narrowly margined green-white, nearest to RHS 157C. Juvenile foliage, abaxial surface — Yellow-green, nearest to RHS 144A, and very narrowly margined green-white, nearest to RHS 157C. Mature foliage, adaxial surface — Nearest to in between green, RHS NN137A, and yellow-green, nearest to RHS 147A; very narrowly margined yellow-green, RHS 144B. Mature foliage, abaxial surface — Yellow-green, nearest to in between RHS 144A and 146B, and very narrowly margined yellow-green, RHS 144B.

*Venation*.—Venation pattern — Pinnate. Color, mature adaxial surface — Yellow-green, nearest to a combination of RHS 144B and 144C. Color, mature abaxial surface — Yellow-green, nearest to RHS 144B.

*Petiole*.—Length — 0.8 cm, on average. Cross-section — Flattened. Average diameter — Horizontal width of 0.6 cm and vertical width of 0.5 cm. Texture, pubescence and luster — Smooth, glabrous; adaxial surface is glossy and the abaxial surface is moderately glossy. Strength — Strong. Color, adaxial surface — Yellow-green, nearest to RHS 144B. Color, abaxial surface — Yellow-green, nearest to RHS 144B.

Inflorescence: No flowering has been observed to date.

Flower bud: No flowering has been observed to date.

Flower: No flowering has been observed to date.

Reproductive organs: No flowering has been observed to date.

Fruit and seed: No flowering has been observed to date.

COMPARISONS WITH THE PARENT PLANT AND CLOSEST KNOWN COMPARATOR

Plants of the new cultivar 'LICLUS02' may be distinguished from its parent, *Clusia rosea* 'Princess', by the characteristics described in Chart 1.

CHART 1

| Characteristic | 'LICLUS02' | 'Princess' |
|---|---|---|
| Growth habit. | Less compact than 'Princess'. | More compact than 'LICLUS02'. |
| Plant height. | Taller than 'Princess'. | Shorter than 'LICLU02'. |
| Leaf size. | Larger than 'Princess'. | Smaller than 'LICLUS02'. |

COMPARISONS WITH THE MOST SIMILAR VARIETY OF COMMON KNOWLEDGE

Plants of the new cultivar 'LICLUS02' are most similar to the commercial variety, *Clusia* 'LICLUS01' (U.S. Plant Pat. No. 28,776). A comparison of 'LICLUS01' with 'LICLUS02' is described in Chart 2.

CHART 2

| Characteristic | 'LICLUS02' | 'LICLUS01' |
|---|---|---|
| Growth habit. | Moderately branched. | Freely branching. |
| Leaf aspect. | 55 degrees to vertical. | 60 degrees to vertical. |
| Leaf size. | Longer than 'LICLUS01'. | Shorter than 'LICLUS02'. |
| General. coloration of mature leaf. | Green to yellow-green; lighter green than 'LICLUS01. | Green; darker green than 'LICLUS02'. |

That which is claimed is:

1. A new and distinct variety of *Clusia rosea* plant named 'LICLUS02', substantially as described and illustrated herein.

* * * * *